US00PP19814P2

(12) United States Plant Patent
Noodelijk

(10) Patent No.: US PP19,814 P2
(45) Date of Patent: Mar. 10, 2009

(54) ***CHRYSANTHEMUM* PLANT NAMED 'GRANO YELLOW'**

(50) Latin Name: *Chrysanthemum morifolium*
Varietal Denomination: Grano Yellow

(76) Inventor: Robert Noodelijk, Vrouwgeestweg 26, Woubrugge (NL), 2481 KN ( * ) Notice: Subject to any disclaimer, the term of this patent is extended or adjusted under 35 U.S.C. 154(b) by 0 days.

(21) Appl. No.: 12/001,099

(22) Filed: Dec. 10, 2007

(51) Int. Cl.
*A01H 5/00* (2006.01)

(52) U.S. Cl. ..... Plt./289

(58) Field of Classification Search ..... Plt./295, Plt./289

See application file for complete search history.

*Primary Examiner*—Kent L Bell
(74) *Attorney, Agent, or Firm*—Jondle & Associates, P.C.

(57) ABSTRACT

A *chrysanthemum* plant named 'Grano Yellow' characterized by large-sized blooms with yellow ray florets and prolific branching, a natural season flowering date of September 15, a blooming period of 7 weeks, a rounded plant habit and a spreading and rapid growth habit, is disclosed.

1 Drawing Sheet

Genus: *chrysanthemum morifolium.*
Variety denomination: 'Grano Yellow'.

BACKGROUND OF THE INVENTION

'Grano Yellow' is a product of a breeding and selection program for outdoor pot mums (garden mums) which had the objective of creating new *chrysanthemum* cultivars with a decorative type inflorescence, a natural season flowering date around September 15 and a blooming period of 7 weeks. The new plant of the present invention comprises a new and distinct cultivar of *chrysanthemum* plant.

'Grano Yellow' is a seedling resulting from the open pollination among groups of un-named and unpatented *chrysanthemum* cultivars maintained under the control of the inventor for breeding purposes. The new and distinct cultivar was discovered and selected as one flowering plant by Robert Noodelijk on a cultivated field in Woubrugge, The Netherlands in September 2005. The plant has been asexually reproduced by cuttings in greenhouses at Woubrugge, The Netherlands over a 2 year period. The new cultivar has been found to retain its distinctive characteristics through successive asexual propagations.

SUMMARY OF THE INVENTION

The following are the most outstanding and distinguishing characteristics of the new cultivar when grown under normal horticultural practices in Woubrugge, The Netherlands.

1. Large yellow inflorescences;
2. A rounded plant habit; and
3. A spreading and rapid growth habit.

DESCRIPTION OF THE PHOTOGRAPHS

The present invention of a new and distinct variety of *chrysanthemum* is shown in the accompanying photographs; the colors shown are as true as can be reasonably obtained by conventional photographic procedures.

DESCRIPTION OF THE INVENTION

Figure 1:
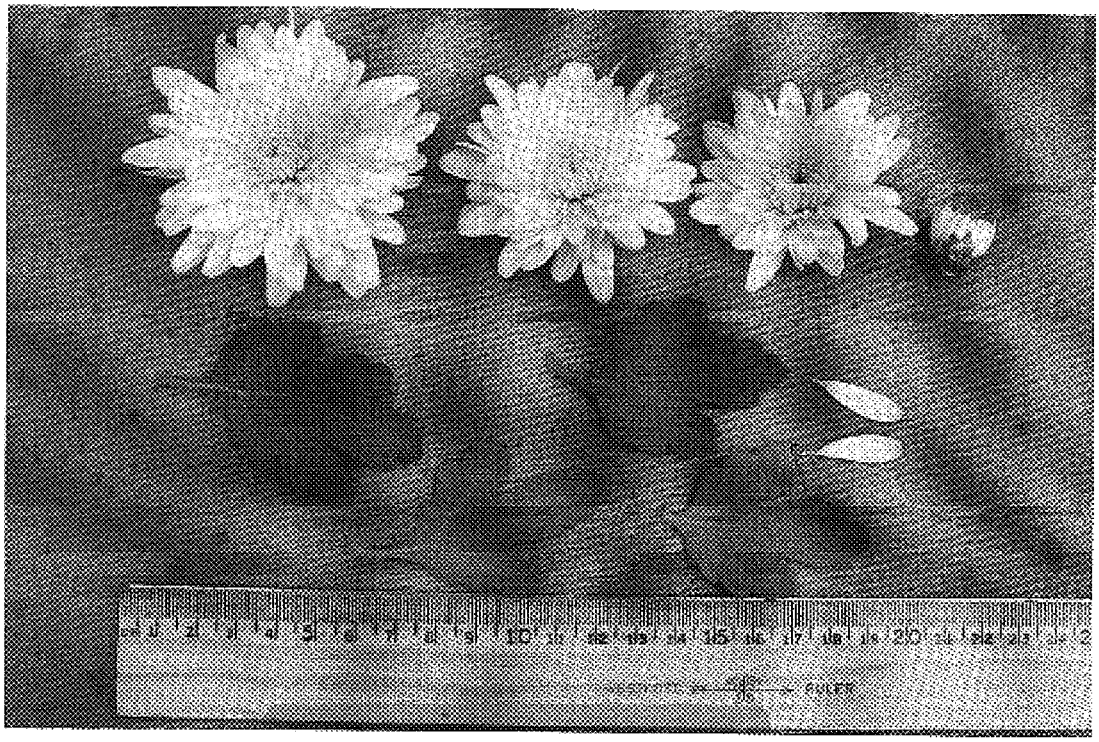
FIG. 1 shows a close-up of the bud, florets, leaves and individual inflorescences.
Figure 2:
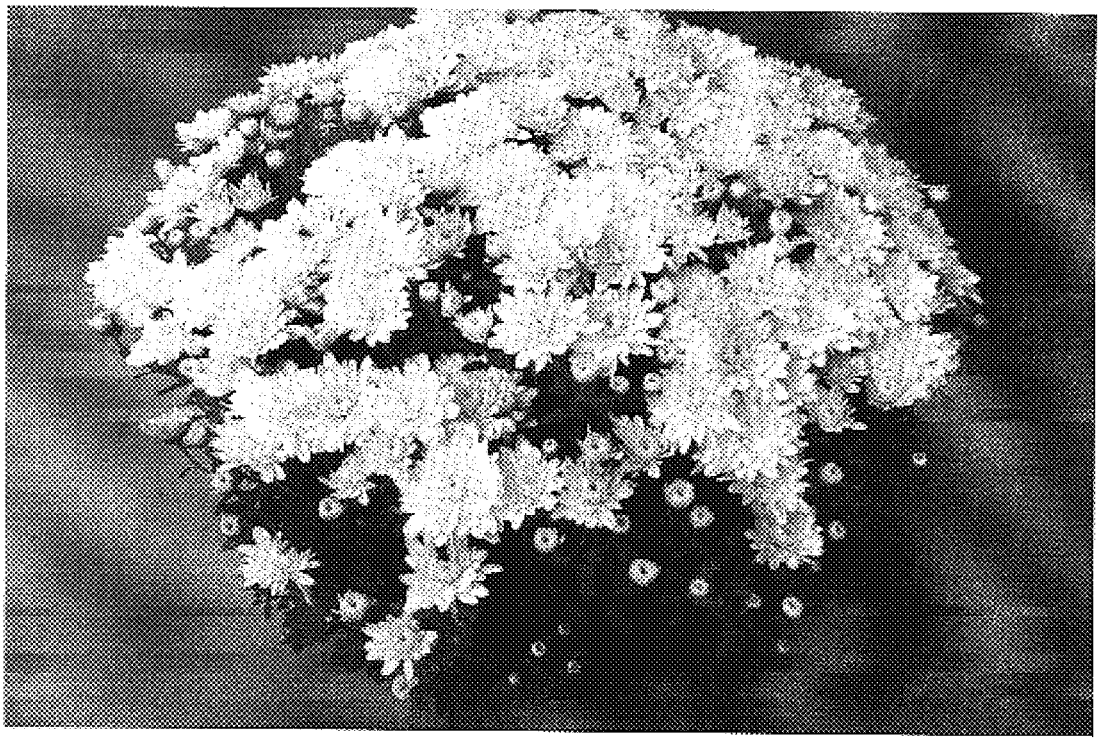
FIG. 2 shows a plant of the cultivar in full bloom.

This new variety of *chrysanthemum* is of the botanical classification *Chrysanthemum morifolium.* The observations and measurements were gathered from plants grown outdoors in Woubrugge, The Netherlands under natural day length and temperature and planted in week 22 in 2005 and 2006. The natural blooming date of this crop was September 15. The average height of the plants was 46 cm. No growth retardants were used. No tests were done on disease or insect resistance or susceptibility. No tests were done on cold or drought tolerance. This new variety produces large-sized blooms with yellow ray florets and a yellow center blooming for a period of 7 weeks.

The following is a description of the plant and characteristics that distinguish 'Grano Yellow' as a new and distinct variety. The color designations are taken from the plant itself. Accordingly, any discrepancies between the color designations and the colors depicted in the photographs are due to photographic tolerances. The color chart used in this description is: The Royal Horticultural Society colour chart, edition 1995.

DETAILED BOTANICAL DESCRIPTION

Plant:
- *Shape.*—Rounded.
- *Growth habit.*—Spreading.
- *Growth rate.*—Rapid.
- *Height.*—45 cm to 48 cm.
- *Width.*—53 cm to 56 cm.

Branches:
- *Stem.*—Color: RHS 137C (green). Strength: Strong. Brittleness: Branches are brittle. Anthocyanin coloration: Absent.
- *Length of lateral branch (from top to bottom).*—17.5 cm to 25 cm.
- *Diameter of lateral branch.*—0.3 cm.
- *Lateral branch color.*—RHS 137C (green).
- *Lateral branch attachment.*—Petiolate.

*Branching* (*average number of lateral branches*).—Very prolific with 11 breaks after pinching.

Leaves:

*Color.*—Upper surface: RHS 137A (green). Lower surface: RHS 137C (green).

*Size.*—General: Medium. Length: 5.5 cm to 6.0 cm. Width: 5.0 cm to 5.5 cm.

*Quantity* (*number per lateral branch*).—7 to 9. Shape: Ovate. Apex: Rounded. Base: Asymmetric. Margin: Crenate. Texture: Upper surface: Glabrous. Lower surface: Pubescent.

*Venation arrangement.*—Palmate.

*Shape of base of sinus between lateral lobes.*—Acute.

*Margin of sinus between lateral lobes.*—Diverging.

Bud:

*Size.*—General: Large. Cross-section: 1.5 cm. Height: 1.5 cm.

*Outside color.*—RHS 9A (yellow).

*Involucral bracts.*—2 rows, length 0.7 cm, width 0.3 cm.

*Involucral bracts among disc-florets.*—Absent.

*Involucral bracts color.*—RHS 138A (green).

Bloom:

*Type.*—Double.

*Size.*—General: Large. Fully expanded: 6.8 cm to 7.5 cm.

*Number of blooms per branch.*—Approximately 5 blooms per branch.

*Performance on the plant* (*blooming period*).—7 weeks.

*Fragrance.*—Typical of *chrysanthemum*; slight.

*Color, center of the inflorescence.*—Immature: RHS 6A (yellow). Mature: RHS 6A (yellow).

*Tonality from distance.*—A garden mum with large yellow inflorescences.

*Discoloration to color.*—None.

*Peduncle length.*—8 cm to 10 cm.

*Peduncle diameter.*—0.2 cm.

*Peduncle color.*—RHS 137C (green).

*Natural season blooming date.*—September 15.

Ray florets:

*Texture.*—Both the upper and lower surfaces are smooth.

*Number.*—170 to 210.

*Cross-section.*—Flat.

*Color.*—Upper surface: RHS 6A (yellow). Lower surface: RHS 6C (yellow).

*Longitudinal axis of majority.*—Straight and reflexing.

*Length of corolla tube.*—0.3 cm.

*Apex.*—Rounded.

*Margin.*—Entire.

*Length.*—2.7 cm to 3.0 cm.

*Width.*—0.9 cm.

*Ratio length/width.*—Medium.

Disc florets: Not present:

Reproductive Organs:

*Stamen* (*present on disc florets only*).—Absent.

*Pollen.*—Absent.

*Style.*—Thin.

*Style color.*—RHS 144A (yellow-green).

*Style length.*—0.5 cm.

*Stigma color.*—RHS 144A (yellow-green).

*Stigma width.*—0.1 cm.

*Ovaries.*—Enclosed in the calyx.

Fruit/Seed set: Seeds are produced in small quantities; ovate, RHS 199A (grey-brown) and 0.15 cm in length.

COMPARISON WITH COMMERCIAL CULTIVARS

'Grano Yellow' differs from the commercial variety 'Gold Crest' (U.S. Plant Pat. No. 11,606) in that 'Grano Yellow' flowers earlier than 'Gold Crest'. Additionally, 'Grano Yellow' has a larger inflorescence size and a more vigorous growth habit than 'Gold Crest'.

I claim:

1. A new and distinct variety of *chrysanthemum* plant as described and illustrated.

* * * * *